United States Patent
Stevens (10) Patent No.: US 9,839,389 B2
(45) Date of Patent: Dec. 12, 2017

(54) FOOT-STRENGTH TEST DEVICE AND METHODS FOR USE

(71) Applicant: Rosalind Franklin University of Medicine and Science, North Chicago, IL (US)

(72) Inventor: Karen Marie Stevens, North Chicago, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 42 days.

(21) Appl. No.: 14/689,550

(22) Filed: Apr. 17, 2015

(65) Prior Publication Data

US 2015/0305664 A1 Oct. 29, 2015

Related U.S. Application Data

(60) Provisional application No. 61/983,241, filed on Apr. 23, 2014.

(51) Int. Cl.
*A61B 5/00* (2006.01)
*A61B 5/22* (2006.01)

(52) U.S. Cl.
CPC .................................. *A61B 5/224* (2013.01)

(58) Field of Classification Search
CPC .......... A61B 5/11; A61B 5/1124; A61B 5/22; A61B 5/224
USPC ........................................ 600/587, 592, 595
See application file for complete search history.

(56) References Cited

U.S. PATENT DOCUMENTS

| | | | | | |
|---|---|---|---|---|---|
| 4,206,636 | A | * | 6/1980 | Hendrix | G01L 1/2206 73/132 |
| 5,402,800 | A | * | 4/1995 | Hollis | A61B 5/103 600/592 |
| 6,110,078 | A | * | 8/2000 | Dyer | A61H 1/0266 482/121 |
| RE40,427 | E | * | 7/2008 | Nashner | A61B 5/0488 600/546 |
| 7,744,546 | B2 | * | 6/2010 | Lee | A61H 1/0237 601/24 |
| 7,976,482 | B2 | * | 7/2011 | Mayr | A61B 5/1071 600/592 |

(Continued)

OTHER PUBLICATIONS

JP 2006-006369, Nakamura et al., Jan. 12, 2006, Japanese patent with English translation.*

(Continued)

*Primary Examiner* — Max Hindenburg
(74) *Attorney, Agent, or Firm* — McDonnell Boehnen Hulbert & Berghoff LLP (57) ABSTRACT

The present disclosure provides a device for testing the strength of a human foot. The device includes a substantially planar member having a top surface and a bottom surface. The device also includes a foot-engaging member moveable along the top surface substantially planar member from a first position to a second position. In addition, the device includes a force sensor fixed with respect to the substantially planar member, where the force sensor resists movement between the first position and the second position. Further, the device includes a tension bearing element connecting the foot-engaging member to the force sensor.

17 Claims, 7 Drawing Sheets

(56) References Cited

U.S. PATENT DOCUMENTS

| 8,753,294 | B2* | 6/2014 | Branch | A61B 5/1071 |
| | | | | 600/592 |
| 9,194,696 | B2* | 11/2015 | Smith | A61B 5/0082 |
| 9,295,422 | B2* | 3/2016 | Tai | A61B 5/222 |
| 9,386,943 | B2* | 7/2016 | Strickland | A61B 5/11 |

OTHER PUBLICATIONS

JP 2008-93186, Yamazaki et al., Apr. 24, 2008, Japanese patent with English translation.*
(1990) Dutton, "Ankle Foot Muscle Anatomy", pp. 954-955 and 975, 977.
Soysa et al., "Importance and challenges of measuring intrinsic foot muscle strength", Journal of Foot and Ankle Research, 5(29):1-14 (2012).

* cited by examiner

FOOT-STRENGTH TEST DEVICE AND METHODS FOR USE

CROSS-REFERENCE TO RELATED APPLICATIONS

This application claims the benefit of the filing date of U.S. Provisional Patent Application Ser. No. 61/983,241, filed Apr. 23, 2014, which is hereby incorporated by reference in its entirety.

BACKGROUND

Unless otherwise indicated herein, the materials described in this section are not prior art to the claims in this application and are not admitted to be prior art by inclusion in this section.

Intrinsic foot muscles contribute to the support of the medial longitudinal arch and work in conjunction with the plantar aponeurosis, plantar ligaments and extrinsic foot muscles to control the stresses on the foot during gait. As such, the strength of intrinsic foot muscles is important in normal functional activities. Weakness of these muscles has been implicated in foot pathology, impaired balance, and addressed in rehabilitation clinical guidelines. Intrinsic foot muscle weakness has also been implicated in the development of pes cavus in Charcot-Marie-Tooth disease (CMT), heel pain, claw toe deformity, hammer toe deformity, and hallux valgus. The level of intrinsic muscle weakness necessary for the development of these deformities and disorders is unknown. To assess the degree of weakness and to determine the effect of strengthening intrinsic muscles, a valid and reliable measure of intrinsic muscle strength is needed. There are diverse methods available for measuring intrinsic muscle properties, but there is lack of agreement regarding the most appropriate measure of strength. Therefore, an improved device and method for measuring intrinsic foot muscle strength may be desired.

SUMMARY

Example devices and methods described herein describe various devices and methods for measuring intrinsic foot muscle strength. Such devices and methods will provide a quantitative measure of foot strength that may be used for screening for prevention, evaluation of patients with lower extremity pathology, and as a variable in lower extremity research studies. While various exercises have been provided to patients to strengthen these muscles, there are no practical devices and methods to quantify the strength of these muscles.

Thus, in one aspect, a device is provided for testing the strength of a human foot. The device includes a substantially planar member having a top surface and a bottom surface. The device also includes a foot-engaging member moveable along the top surface substantially planar member from a first position to a second position. In addition, the device includes a force sensor fixed with respect to the substantially planar member, where the force sensor resists movement between the first position and the second position. Further, the device includes a tension bearing element connecting the foot-engaging member to the force sensor.

In a second aspect, a method is provided for testing the strength of a human foot. The method may include (a) positioning the human foot on a top surface of a substantially planar member, (b) engaging one or more toes of the human foot with a foot-engaging member, wherein the foot-engaging member is moveable along the top surface substantially planar member from a first position to a second position, and wherein a tension bearing element connects the foot-engaging member to a force sensor, (c) while a heel of the human foot is stationary on the top surface of the substantially planar member, moving the one or more toes of the human foot from the first position to the second position, and (d) recording a peak force detected by the force sensor.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, with respect to measurements, "about" means +/−5%.

As used herein, the term "coefficient of static friction" means the ratio of the force of friction between an object and a surface to the frictional force resisting the motion of the object when the object is at rest.

As used herein, the term "coefficient of kinetic friction" means the ratio of the force of friction between an object and a surface to the frictional force resisting the motion of the object when the object is moving.

As used herein, the term "peak force" means the highest value of recorded by a force sensor during a particular trial.

As used herein, the term "average force" means a magnitude of force over a given time period ($t_0$-$t_1$) during a particular trial.

The present disclosure provides devices and methods for testing the strength of a human foot. As discussed above, such devices and methods may provide insight into the intrinsic foot muscle function in patients with foot and ankle disorders. As such, the device may be used to record baseline strength of the intrinsic muscles of the foot. As the patient performs various therapy and treatment to increase strength, the baseline measurements can be used as a point of comparison for future measurements using the device.

Figure 1A:
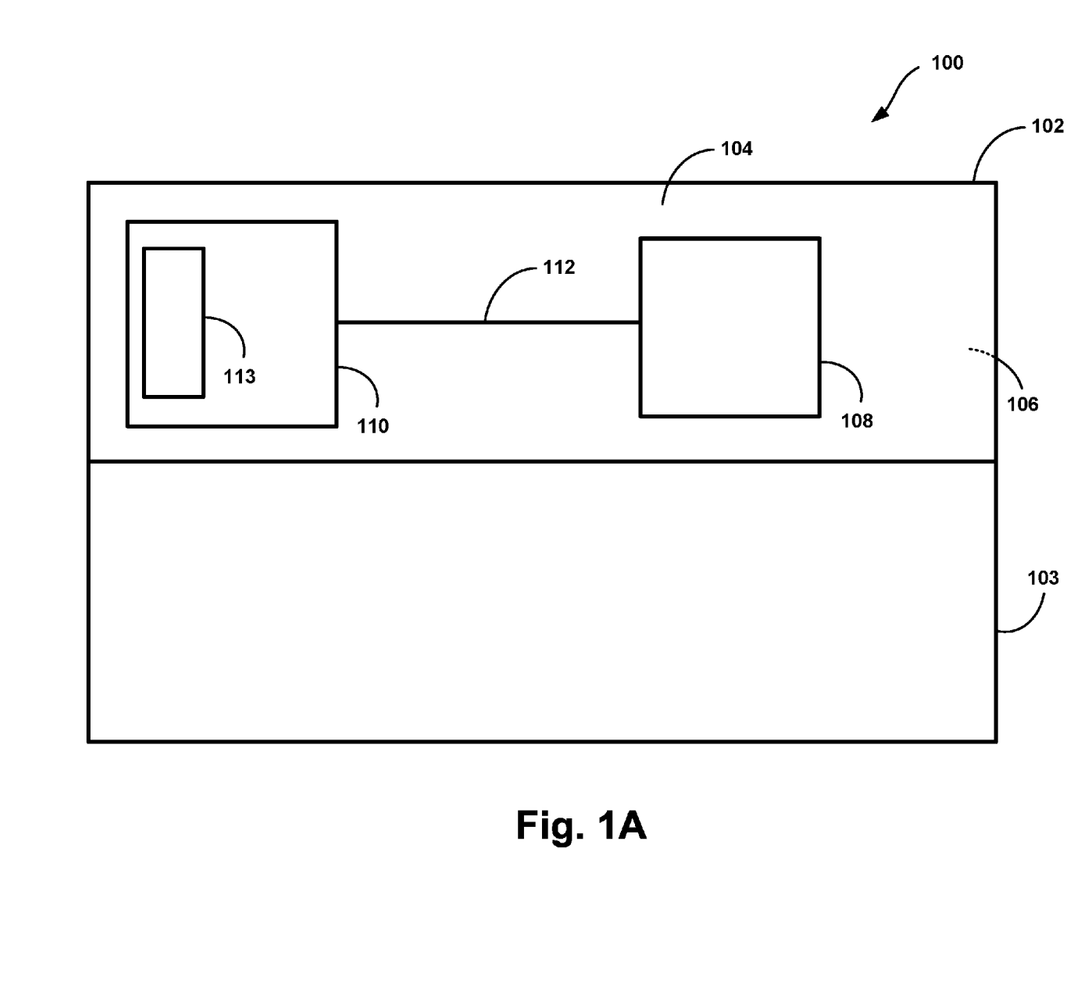
FIG. 1A is a top view of a device for testing the strength of a human foot, according to an example embodiment.
Figure 1B:
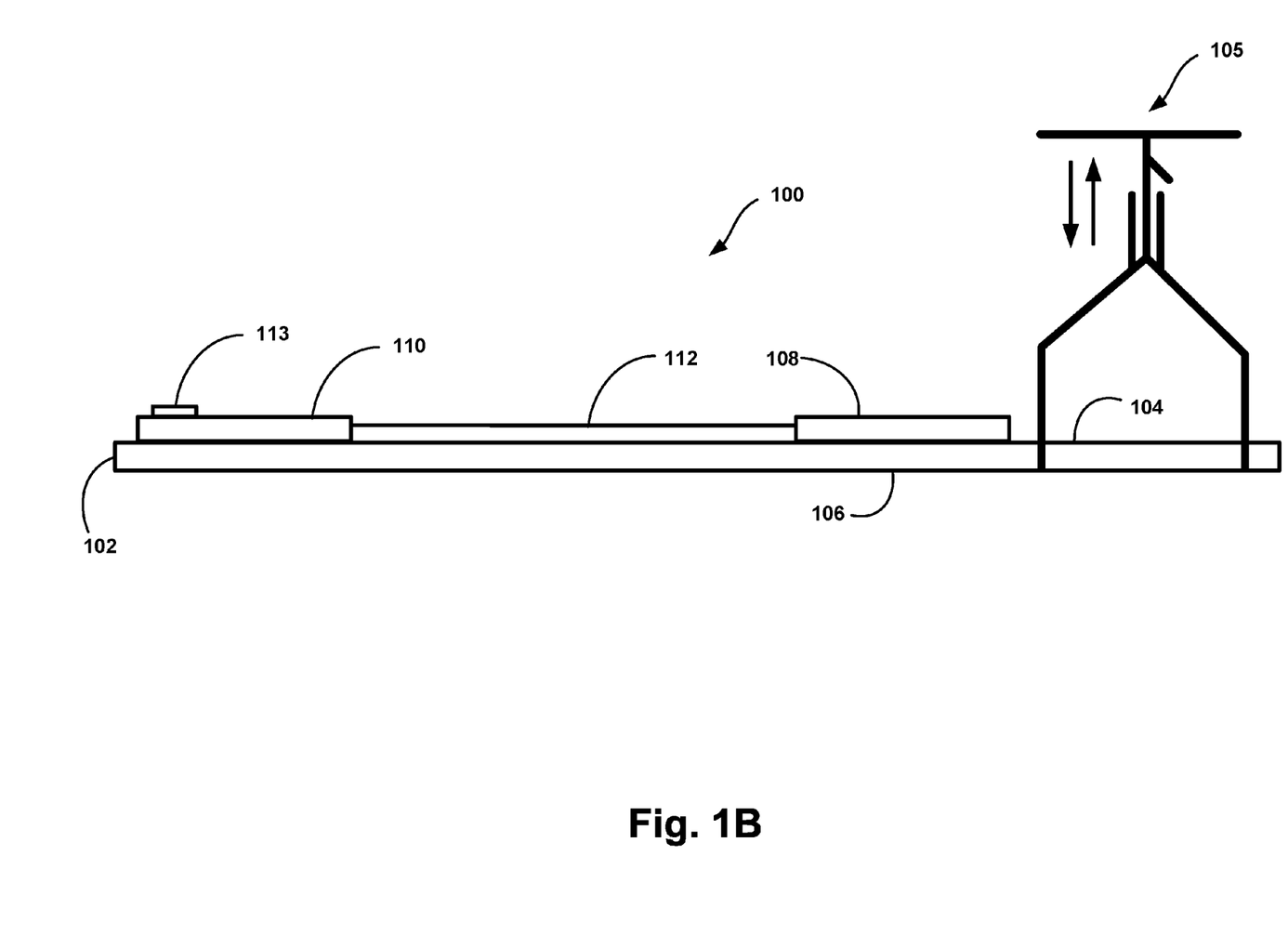
FIG. 1B is a side view of a device for testing the strength of a human foot, according to an example embodiment.

With reference to the Figures, FIG. 1A illustrates an example foot-strength testing device 100. The device 100 may include a substantially planar member 102 having a top surface 104 and a bottom surface 106. The device 100 may also include a foot-engaging member 108, a force sensor 110 fixed with respect to the substantially planar member 102, and a tension bearing element 112 connecting the foot-engaging member 108 to the force sensor 110. The foot-engaging member 108 is moveable along the top surface 104 from a first position to a second position, where the foot-engaging member 108 is closer to the force sensor 110 in the first position than in the second position. As such, a force applied to the force sensor 110 increases as the distance between the foot-engaging member 108 and the force sensor 100 increases. In addition, as shown in FIG. 1B, the device 100 may include an adjustable seat 105 positioned over the substantially planar member 102. The seat may be adjustable in height to accommodate a variety of patient heights.

The substantially planar member 102 may have a length in the range of about 18 inches to 48 inches, and a width in the range of about 4 inches to about 12 inches. In one example, the substantially planar member 102 may be foldable. For example, the substantially planar member 102 may include a hinge on the bottom surface 106, such that the substantially planar member 102 is configured to fold in half for storage. In another example, the substantially planar member 102 may include a cutout for a hand grip for easy portability. In addition, the top surface 104 of the substantially planar member 102 has a low coefficient of kinetic friction. For example, the top surface 104 may include a melamine resin, Polytetrafluoroethylene (PTFE), plastic, metal, tempered glass, and/or composite material. As such, the top surface 104 has a coefficient of kinetic friction ($\mu_k$) less than about 0.5. In contrast, the bottom surface 106 of the substantially planar member 102 may have a high coefficient of static friction. For example, the bottom surface 106 may include rubber, silicone gel, wood, metal, and/or composite material. As such, the bottom surface 106 has a coefficient of static friction ($\mu_s$) greater than about 0.5. In another example, the bottom surface 106 may be the same material as the top surface 104, but the bottom surface 106 may include one or more gripping elements positioned on the bottom surface 106. In one specific example, there may be four gripping elements positioned at four corners of the bottom surface 106. Such gripping elements may be materials that have a high coefficient of static friction, such as rubber, silicone gel, wood, metal, and/or composite material. Such gripping elements may have a coefficient of static friction ($\mu_s$) greater than about 0.5. In addition, the top surface 104 of the substantially planar member 102 may include one or more markings to indicate a location for heel and or toe placement of a foot being tested.

In another example, the device 100 may further include a second substantially planar member 103 positioned adjacent to the substantially planar member 102. In such an example, the second substantially planar member 103 has a thickness equal to the thickness of the substantially planar member 102, such that both feet of a user are level when using the device 100. The second substantially planar member 103 may be coupled to the substantially planar member 102 via a hinge, for example. In another example, the second substantially planar member 103 may not be attached to the substantially planar member 102.

Figure 2:
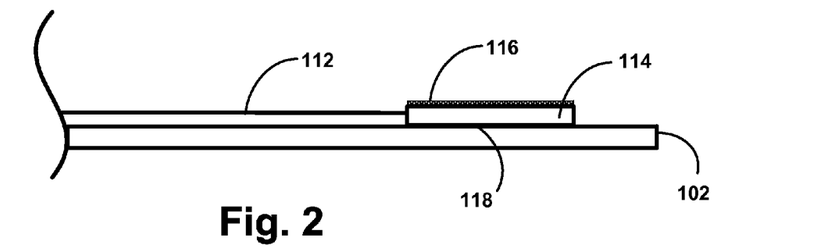
FIG. 2 is a side view of an example foot-engaging member, according to an example embodiment.

The foot-engaging member 108 enables a user of the device 100 to apply a tension force, via the tension bearing element 112, to the force sensor 110 using the user's toes and intrinsic muscles of the feet. As such, the foot-engaging member 108 may take various forms. In one example, the foot-engaging member 108 comprises a cloth 114, as shown in FIG. 2. In such an example, the cloth 114 may include a grommet for attaching to the tension bearing element 112. The cloth 114 is dimensioned to underlie a portion of a user's forefoot. As such, the cloth 114 may be generally rectangular, with a width in the range of about 3 inches to about 6 inches, and a length in the range of about 4 inches to about 8 inches. A top surface 116 of the cloth 114 may include a gripping surface, for example including a rubber or other material with a high coefficient of static friction. In contrast, the bottom surface 118 of the cloth 114 may include a material with a low coefficient of kinetic friction such that the cloth 114 slides easily along the top surface 104 of the substantially planar member 102. In operation, the first metatarsal head of a user's foot may be aligned with the end of the cloth 114 furthest away from the force sensor 110. In this position, the tension bearing element 112 may be pulled so that there is no slack. The user may then pull on the cloth 114 with their toes and forefoot from the first position to the second position while keeping their heel in a stationary position on the substantially planar member 102. The force applied to the cloth 114 is transferred, via the tension bearing element 112, to the force sensor 110 and the peak force detected by the force sensor 110 may be recorded. In addition, the force sensor 110 may further determine a time to reach the peak force, an average force, the peak force over time, the work exerted on the cloth 114, and power, among other measurements.

Figure 3:
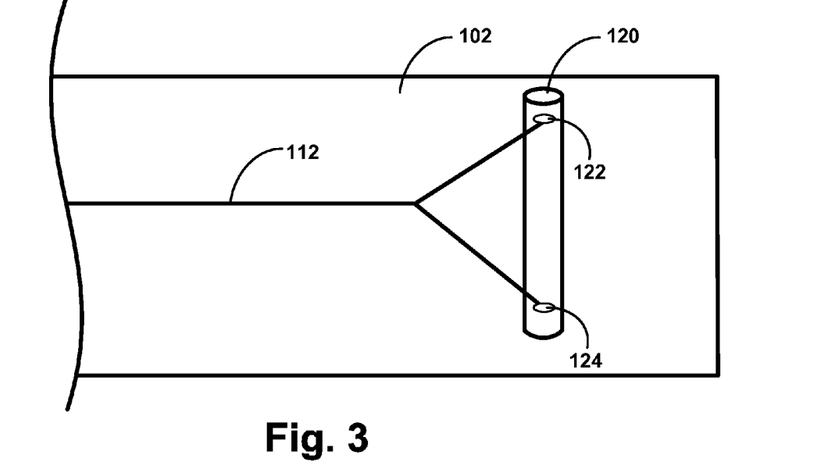
FIG. 3 is a top view of another example foot-engaging member, according to an example embodiment.

In another example, the foot-engaging member 108 comprises a dowel rod 120, as shown in FIG. 3. The dowel rod 120 may include a hole 122, 124 at each end of the dowel rod for connecting to the tension bearing element 112. The dowel rod 120 may be dimensioned such that a user can position their foot between the two holes 122, 124 and grab the dowel rod 120 using their toes. As such, the dowel rod 120 may have a length in the range of about 4 inches to about 8 inches, and a diameter in the range of about 0.25 inches to about 2 inches. In operation, the user may position their toes around the dowel rod 120. In this position, the tension bearing element 112 may be pulled so that there is no slack. The user may then pull on the dowel rod 120 with their toes from the first position to the second position while keeping their heel in a stationary position on the substantially planar member 102. The force applied to the dowel rod 120 is transferred, via the tension bearing element 112, to the force sensor 110 and the peak force detected by the force sensor 110 may be recorded. In addition, as discussed above, the force sensor 110 may further determine a time to reach the peak force, an average force, the peak force over time, the work exerted on the dowel rod 120, and power, among other measurements.

Figure 4:
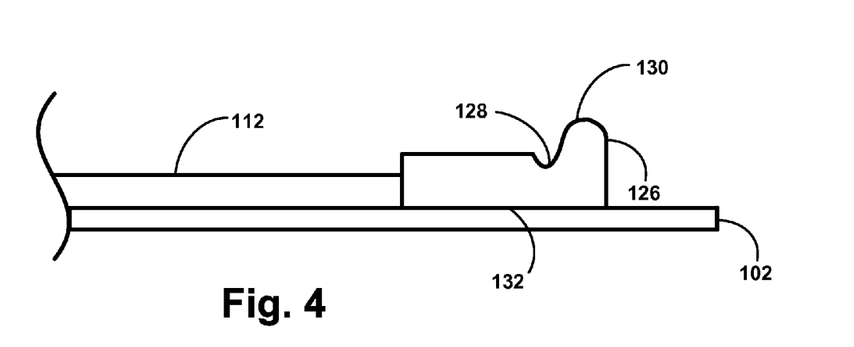
FIG. 4 is a side view of another example foot-engaging member, according to an example embodiment.

In another example, the foot-engaging member 108 comprises a molded plastic component 126, as shown in FIG. 4. The molded plastic component 126 may include one or more indentations 128 to receive the toes of the foot being tested. In one particular example, the molded plastic component 126 may include two indentations, one for the big toe and one for the remaining toes. In another example, the molded plastic component 126 may include a single indentation extending the width of the molded plastic component 126 for all of the toes of the user. At least a portion of the top surface 130 of the molded plastic component 126 may include a gripping surface, for example including a rubber or other material with a high coefficient of static friction. In contrast, the bottom surface 132 of the molded plastic component 126 may include a material with a low coefficient of kinetic friction such that the molded plastic component 126 easily along the top surface 104 of the substantially planar member 102. In operation, the user's toes may be positioned in the one or more indentations 128 of the molded plastic component 126. In this position, the tension bearing element 112 may be pulled so that there is no slack. The user may then pull on the molded plastic component 126 with their toes from the first position to the second position while keeping their heel in a stationary position on the substantially planar member 102. The force applied to the molded plastic component 126 is transferred, via the tension bearing element 112, to the force sensor 110 and the peak force detected by the force sensor 110 may be recorded. In addition, as discussed above, the force sensor 110 may further determine a time to reach the peak force, an average force, the peak force over time, the work exerted on the molded plastic component 126, and power, among other measurements.

Figure 5A:
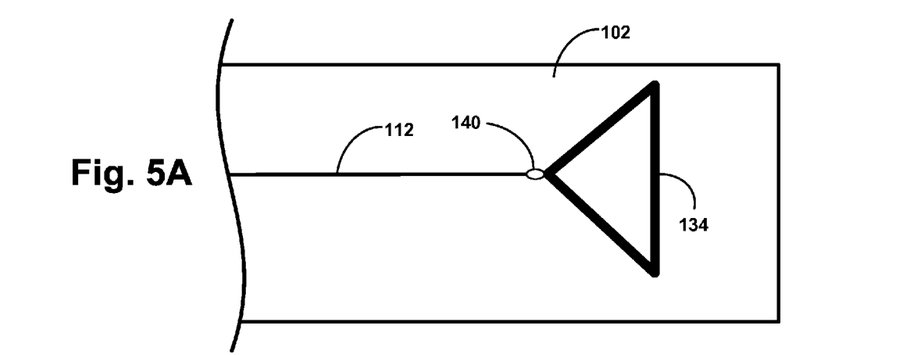
FIG. 5A is a top view of another example foot-engaging member, according to an example embodiment.
Figure 5B:
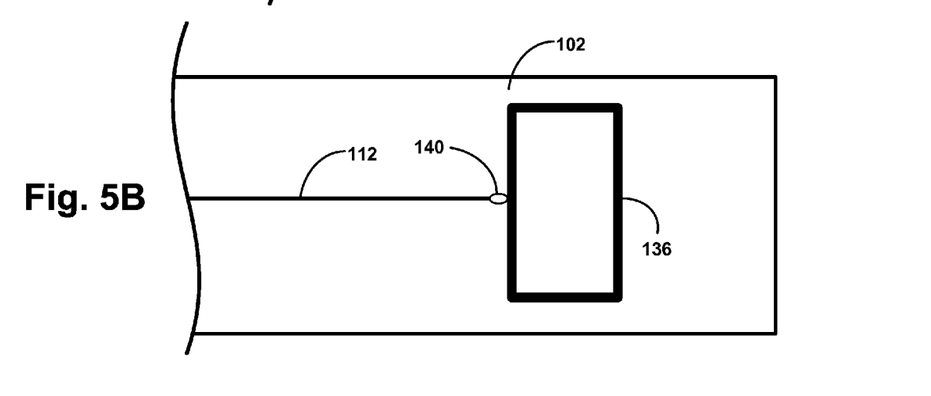
FIG. 5B is a top view of another example foot-engaging member, according to an example embodiment.
Figure 5C:
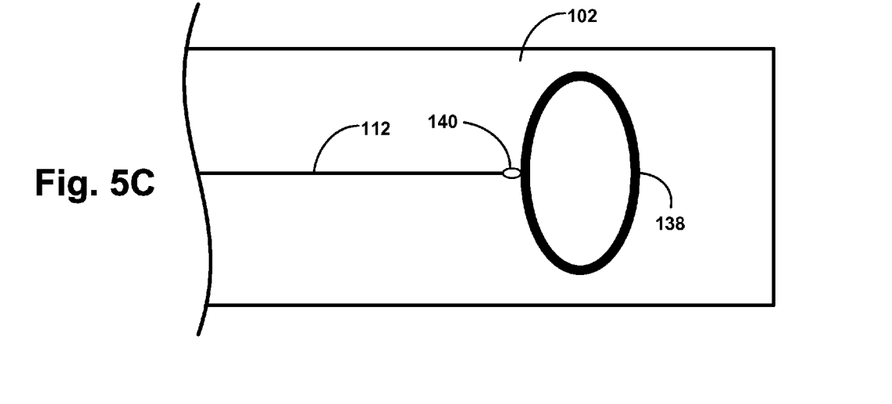
FIG. 5C is a top view of yet another example foot-engaging member, according to an example embodiment.

In yet another example, the foot-engaging member 108 comprises a shape including a cutout in the center of the shape. The shape including the cutout may take various forms. In one example, as shown in FIG. 5A, the shape may be a triangular foot-engaging member 134. In another example, as shown in FIG. 5B, the shape may be a rectangular foot-engaging member 136. In yet another example, as shown in FIG. 5C, the shape may be an elliptical foot-engaging member 138. Other shapes are possible as well. Each of the foot-engaging members may be metal, plastic, metal with a plastic coating, wood, and/or composite material. Further, as illustrated in FIGS. 5A-5C, each of the foot-engaging members may include an eyelet 140 used to couple the foot-engaging member to the tension bearing element 112. In another example, the tension bearing element 112 is coupled directly to the foot-engaging member.

The force sensor 110 is fixed with respect to the substantially planar member 102. In one example, as shown in FIG. 1A, the force sensor 110 is fixed to the top surface 104 of the substantially planar member 102. In another example, the force sensor 110 is fixed to the ground adjacent to the substantially planar member 102. Other examples are possible as well.

The force sensor 110 may be configured to apply tension to the foot-engaging member 108, such that the tension increases with the distance displaced from the force sensor 110. The force sensor 110 may use a spring, a moveable weight, a piston, or another mechanism to generate force in a direction toward the force sensor 110. In one example, the force sensor 110 may be a mechanical force gauge, such as a spring scale. The spring scale may include a moveable indicator that moves as the spring is displaced from its relaxed position. Once a peak force is reached, the indicator remains in the position corresponding to the peak force, and a user can determine the peak force by comparing the position of the indicator and scale markings positioned on the spring scale. In another example, the force sensor 110 may be a digital force gauge. Such a digital scale may include a load cell, electrical components, software and a display. The load cell is an electronic device that is used to convert a force into an electrical signal. Through a mechanical arrangement, the force being sensed deforms a strain gauge. The strain gauge converts the deformation (strain) to electrical signals. The software and electronics of the digital force gauge convert the voltage of the load cell into a force value. In one example, the force sensor 110 includes a display 113 to provide a visual display of the force applied to the foot-engaging member 108. In addition, as discussed above, the display 113 may further provide a visual display of a time to reach the peak force, an average force, the peak force over time, the work exerted on the tension bearing element 112, and power, among other measurements made by the force sensor 110.

As discussed above, the force sensor 110 is coupled to the foot-engaging member via a tension bearing element 112. As such, as the foot-engaging member moves from the first position to the second position, the tension bearing element transfers the force applied to the foot-engaging member 108 to the force sensor 110. The tension bearing element 112 may include a cable, a chord, a belt or a band, as examples. In one example, the tension bearing element 112 includes a coupling mechanism between the force sensor 110 and the foot-engaging member 108, such that the foot-engaging member 108 may be detachable from the tension bearing element 112. As such, a physician may be able to easily switch between various foot-engaging members 108, such as between the cloth 114 and the dowel rod 120, as an example. The coupling mechanism may take various forms. In one example, the tension bearing element 112 may include an eyelet at the end closest to the foot-engaging member 108, and a second tension bearing element connected to the foot-engaging member 108 may include a complementary hook or clasp to connect the tension bearing element 112 to the second tension bearing element. In another example, the tension bearing element 112 may include a threaded rod at the end closest to the foot-engaging member 108, and the second tension bearing element connected to the foot-engaging member 108 may include a complementary female threaded port to receive the threaded rod. Other example coupling mechanisms are possible as well.

Figure 1C:
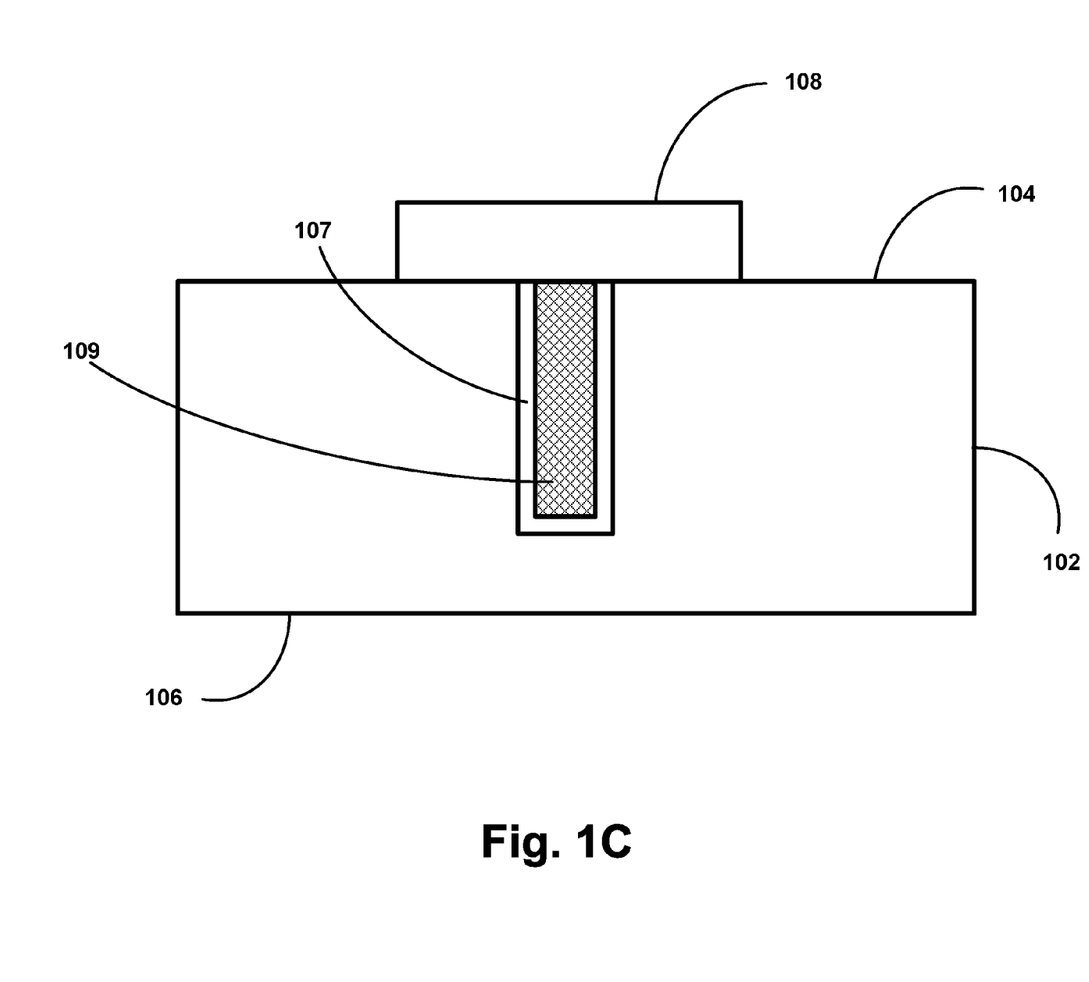
FIG. 1C is a cross-section rear view of an example foot engaging member, according to an example embodiment.

In another example, as shown in FIG. 1C, the device 100 may further include a recessed track 107 on the top surface 104 of the substantially planar member 102, and a complementary flange 109 on a bottom surface of the foot-engaging member 108. The complementary flange 109 may be positioned within the recessed track 107 such that the foot-engaging member 108 moves along the recessed track 107 from the first position to the second position. The recessed track 107 may prevent the foot-engaging member 108 from moving in a lateral (e.g., side-to-side) direction as a user moves the foot-engaging member 108 from the first position to the second position.

Figure 6:
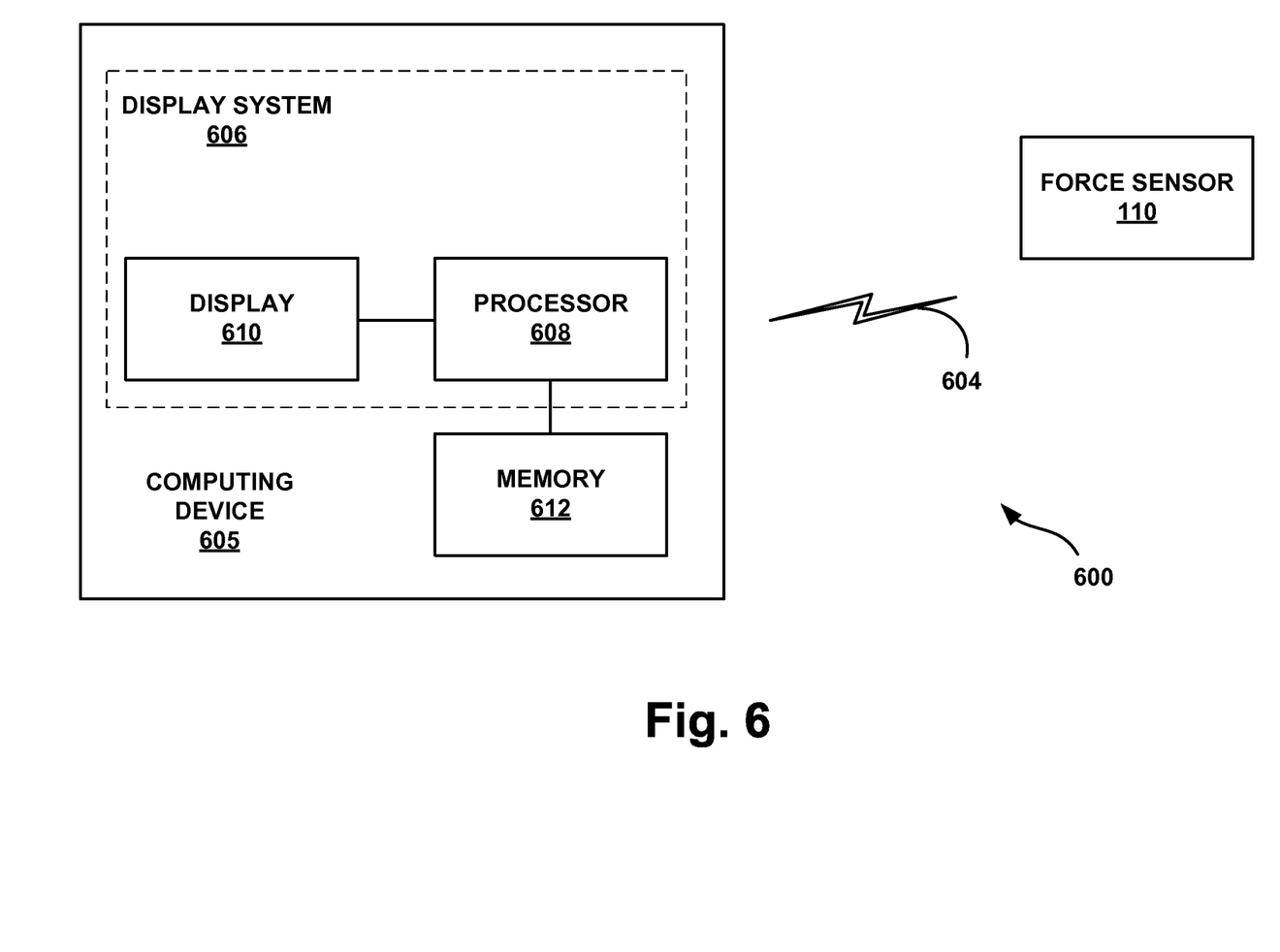
FIG. 6 is a schematic drawing of a computer network infrastructure, according to an example embodiment.

FIG. 6 illustrates an example schematic drawing of a computer network infrastructure. In one system 600, a computing device 602 communicates with the force sensor 110 using a communication link 604, such as a wired or wireless connection. The computing device 602 may be any type of device that can receive data and display information corresponding to or associated with the data. For example, the computing device 602 may be a mobile phone, a tablet, or a personal computer as examples.

Thus, the computing device 602 may include a display system 606 comprising a processor 608 and a display 610. The display 610 may be, for example, an optical see-through display, an optical see-around display, or a video see-through display. The processor 608 may receive data from the force sensor 110, and configure the data for display on the display 610. Depending on the desired configuration, processor 608 can be any type of processor including, but not limited to, a microprocessor, a microcontroller, a digital signal processor, or any combination thereof.

The computing device 602 may further include on-board data storage, such as memory 612 coupled to the processor 608. The memory 612 may store software that can be accessed and executed by the processor 608, for example. The memory 612 can include any type of memory now known or later developed including but not limited to volatile memory (such as RAM), non-volatile memory (such as ROM, flash memory, etc.) or any combination thereof.

According to an example embodiment, the computing device 602 may include program instructions that are stored in the memory 612 (and/or possibly in another data-storage medium) and executable by the processor 608 to facilitate the various functions described herein. Although various components of the system 600 are shown as distributed components, it should be understood that any of such components may be physically integrated and/or distributed according to the desired configuration of the computing system.

The force sensor 110 and the computing device 600 may contain hardware to enable the communication link 604, such as processors, transmitters, receivers, antennas, etc.

In FIG. 6, the communication link 604 is illustrated as a wireless connection; however, wired connections may also be used. For example, the communication link 604 may be a wired link via a serial bus such as a universal serial bus or a parallel bus. A wired connection may be a proprietary connection as well. The communication link 604 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

Figure 7:
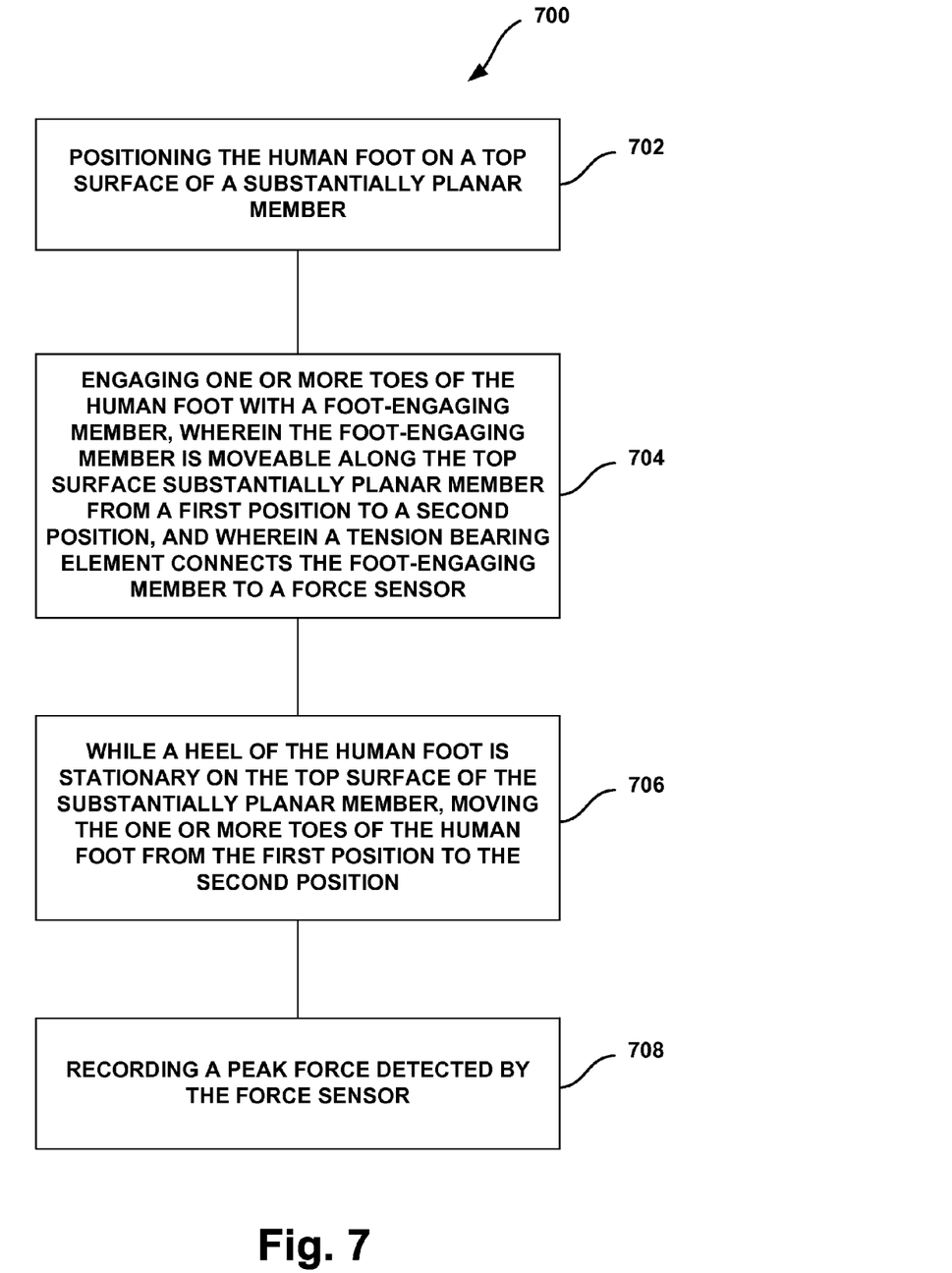
FIG. 7 is a flowchart illustrating an example method according to an example embodiment.

FIG. 7 is a block diagram of an example method for adjusting a fluid flow rate through a fluidic control device. Method 700 shown in FIG. 7 presents an embodiment of a method that could be used by the device 100 of FIGS. 1-6, as an example. Method 700 may include one or more operations, functions, or actions as illustrated by one or more of blocks 702-708. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 700 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 702, the method 700 includes positioning the human foot on a top surface of a substantially planar member. As discussed above, the top surface of the substantially planar member may include one or more markings to indicate a location for heel placement of the foot being tested. At block 704, the method 700 includes engaging one or more toes of the human foot with a foot-engaging member, wherein the foot-engaging member is moveable along the top surface substantially planar member from a first position to a second position, and wherein a tension bearing element connects the foot-engaging member to a force sensor. The foot-engaging member may take various forms, as discussed above in relation to FIGS. 2-5C. At block 706, the method 700 includes moving the one or more toes of the human foot from the first position to the second position while a heel of the human foot is stationary on the top surface of the substantially planar member. At block 708, the method 700 includes recording a peak force detected by the force sensor. As discussed above, the peak force detected by the force sensor may be recorded manually, or the force sensor may transmit the detected peak force to a computing device. In addition, as discussed above, the force sensor may further determine a time to reach the peak force, an average force, the peak force over time, the work exerted on the tension bearing element, and power, among other measurements. In such an example, the method 700 may further include recording one or more of these measurements. Such measurements may be useful in determining patient fatigue, for example.

In one example, the method may further include repeating steps 702-708 two additional times to record three values of peak force. The three values may then be averaged to determine a mean value for peak force. These steps may be repeated for each foot of the user. Further, the user may perform steps 702-708 in a seated position, and may then repeat steps 702-708 in a standing position. In addition, steps 702-708 of method 700 may be performed when a user is in a position of maximum foot pronation. In another example, steps 702-708 of method 700 may be performed when a user is in a position of maximum foot supination. Other examples are possible as well.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

What is claimed is:

1. A device, comprising:
   a substantially planar member having a top surface and a bottom surface;
   a foot-engaging member moveable along the top surface of the substantially planar member from a first position to a second position;
   a force sensor fixed with respect to the substantially planar member, wherein the force sensor measures a force by detecting movement of the foot-engaging member between the first position and the second position;
   a tension bearing element connecting the foot-engaging member to the force sensor;
   a recessed track on the top surface of the substantially planar member; and
   a complementary flange on the foot-engaging member, wherein the complementary flange is positioned within the recessed track such that the foot-engaging member moves along the recessed track from the first position to the second position.

2. The device of claim 1, wherein the foot-engaging member is closer to the force sensor in the first position than in the second position.

3. The device of claim 1, wherein the force sensor is fixed to the top surface of the substantially planar member.

4. The device of claim 1, wherein the top surface of the substantially planar member has a low coefficient of kinetic friction.

5. The device of claim 1, wherein the bottom surface of the substantially planar member has a high coefficient of static friction.

6. The device of claim 1, wherein the top surface of the substantially planar member includes one or more markings to indicate a location for heel placement of a foot being tested.

7. The device of claim 1, further comprising:
   a display on the force sensor to provide a visual display of an amount of force applied to the foot-engaging member.

8. The device of claim 1, wherein the foot-engaging member comprises a cloth.

9. The device of claim 8, wherein the cloth includes a grommet for attaching to the tension bearing element.

10. The device of claim 1, wherein the foot-engaging member comprises a molded plastic component, wherein the molded plastic component includes one or more indentations to receive the toes of a foot being tested.

11. The device of claim 1, wherein the tension bearing element includes a coupling mechanism between the force sensor and the foot-engaging member, such that the foot-engaging member is detachable from the tension bearing element.

12. The device of claim 1, further comprising:
    a second substantially planar member positioned adjacent to the substantially planar member.

13. The device of claim 1, further comprising:
    an adjustable seat positioned over the substantially planar member.

14. A method for testing the strength of a human foot, comprising:
    positioning the human foot on the top surface of the substantially planar member of the device of claim 1;
    engaging one or more toes of the human foot with the foot-engaging member;
    while a heel of the human foot is stationary on the top surface of the substantially planar member, moving the one or more toes of the human foot from the first position to the second position; and
    recording a peak force detected by the force sensor.

15. The method of claim 14, wherein the peak force detected by the force sensor comprises a first trial, the method further comprising:
    while the heel of the human foot is stationary on the top surface of the substantially planar member, moving the one or more toes of the human foot from the first position to the second position to thereby perform a second trial;
    recording a peak force detected by the force sensor for the second trial;
    while the heel of the human foot is stationary on the top surface of the substantially planar member, moving the one or more toes of the human foot from the first position to the second position to thereby perform a third trial;
    recording a peak force detected by the force sensor for the third trial; and
    averaging the peak force detected by the force sensor for each of the first trial, the second trial, and the third trial.

16. The method of claim 14, wherein a user is sitting when performing the method.

17. The method of claim 14, wherein a user is standing when performing the method.

* * * * *